(12) United States Patent
Mu et al.

(10) Patent No.: US 6,368,996 B1
(45) Date of Patent: Apr. 9, 2002

(54) HYDROGENATION CATALYST AND ITS PREPARATION

(75) Inventors: Xuhong Mu; Baoning Zong; Enze Min; Xuan Wang; Ying Wang; Xiaoxin Zhang; Xingtian Shu, all of Beijing (CN)

(73) Assignees: China Petroleum Corporation; Research Institute of Petroleum Processing, Sinopec, both of Beijing (CN)

( * ) Notice: Subject to any disclaimer, the term of this patent is extended or adjusted under 35 U.S.C. 154(b) by 0 days.

(21) Appl. No.: 09/560,444

(22) Filed: Apr. 28, 2000

(30) Foreign Application Priority Data

Apr. 29, 1999 (CN) .......................................... 99 1 06166

(51) Int. Cl.⁷ ........................... B01J 25/00; B01J 23/00; B01J 25/02; C21D 1/04; C22C 27/06
(52) U.S. Cl. ....................... 502/301; 502/314; 502/315; 502/316; 502/319; 502/321; 502/323; 502/324; 148/403; 148/561
(58) Field of Search ................................ 148/561, 403; 502/301, 314–316, 319–324

(56) References Cited

U.S. PATENT DOCUMENTS

| | | | | |
|---|---|---|---|---|
| 3,615,215 A | * | 10/1971 | Von Dohren et al. | 502/301 |
| 3,809,658 A | * | 5/1974 | Csuros et al. | 502/301 |
| 3,839,011 A | | 10/1974 | Larson, Jr. | 75/0.5 BA |
| 3,862,911 A | * | 1/1975 | Chabert | 502/301 |
| 3,986,867 A | * | 10/1976 | Masumoto et al. | 75/126 A |
| 3,997,478 A | * | 12/1976 | Petro | 502/301 |
| 4,052,201 A | * | 10/1977 | Polk et al. | 75/124 |
| 4,255,189 A | * | 3/1981 | Ray | 75/123 B |
| 5,015,993 A | * | 5/1991 | Strom-Olsen et al. | 340/551 |
| 5,090,997 A | | 2/1992 | Birkenstock et al. | 75/338 |
| 5,439,859 A | * | 8/1995 | Durante et al. | 502/66 |
| 5,536,694 A | * | 7/1996 | Schuetz et al. | 502/301 |
| 5,554,573 A | * | 9/1996 | Cordier et al. | 502/301 |
| 5,776,264 A | * | 7/1998 | McCandlish et al. | 148/237 |
| 5,801,286 A | * | 9/1998 | Besson et al. | 564/490 |
| 5,840,989 A | * | 11/1998 | Cordier et al. | 564/490 |
| 5,858,131 A | * | 1/1999 | Inoue et al. | 148/103 |
| 5,896,642 A | * | 4/1999 | Peker et al. | 29/522.1 |
| 6,037,306 A | * | 3/2000 | Xia et al. | 502/315 |
| 6,087,296 A | * | 7/2000 | Harper | 502/301 |

FOREIGN PATENT DOCUMENTS

| | | |
|---|---|---|
| CN | 1073726 A | 6/1993 |
| CN | 1146443 A | 4/1997 |
| CN | 1152475 A | 6/1997 |

\* cited by examiner

*Primary Examiner*—Mark L. Bell
*Assistant Examiner*—Patricia L. Hailey
(74) *Attorney, Agent, or Firm*—Morrison & Foerster LLP

(57) ABSTRACT

An amorphous alloy catalyst for hydrogenation and its preparation method are disclosed herein. The catalyst essentially consists of nickel ranging between 60 and 98 wt %, iron ranging between 0 and 20 wt %, one doping metal element selected from the group consisting of chromium, cobalt, molybdenum, manganese and tungsten ranging between 0 and 20 wt %, and aluminum ranging between 0.5 and 30 wt % based on the weight of said catalyst, wherein the weight percentages of iron and the doping metal element component may not be zero at the same time; and just one broad diffusion peak appears at about $2\theta=45\pm1°$ on the XRD patterns of the catalyst within $2\theta$ range from 20 to 80°. The catalyst herein can be used in processes for hydrogenation of unsaturated compounds such as olefin, alkyne, aromatics, nitro, carbonyl groups, nitrile and soon, and for hydrorefining of caprolactam in particular.

12 Claims, 2 Drawing Sheets

HYDROGENATION CATALYST AND ITS PREPARATION

FIELD OF THE INVENTION

The present invention relates to a hydrogenation catalyst and its preparation.

BACKGROUND OF THE INVENTION

The hydrogenation has been extensively applied in processes such as the hydrogenation of olefin, alkyne, aromatics, nitro compounds, carbonyl groups, nitrile groups and other unsaturated compounds, and hydrorefining of crude products such as caprolactam in chemical, especially fine chemical, engineering field. The most widely used catalyst in these processes is skeletal nickel (Raney nickel) catalyst which has been applied in the industry for many years and has become technically matured, and so long no other catalyst can substitute for it. In recent years, a widely reported amorphous alloy catalyst has shown its superiority to Raney nickel catalyst in respect of activity and selectivity with the momentum of taking the place of Raney nickel catalyst.

Amorphous alloys are a new kind of catalyst materials in which the atoms are in short-range ordered but long-range disordered arrangements, thus ensuring that the catalysts have an increased number of active sites in a uniform distribution. However, ordinary amorphous alloys have the disadvantage of low activity and small specific surface area, which cannot exceed 10 $m^2/g$ even after various chemical and physical treatments, thus its prospect of industrial application is limited. In this connection, CN1073726A discloses a process for the preparation of a large-surface-area Ni(Fe or Co)—Re—P amorphous alloy catalyst by alloying nickel or Fe or Co—Re—P and aluminum using the rapid quenching and moulding method and then leaching out the aluminum with alkali to obtain an amorphous alloy catalyst having a specific surface area of up to 50–130 $m^2/g$ which make it possible to be used in industry. In comparison with Raney nickel catalyst, the Re—Ni—P catalyst has a distinctly higher activity in the saturation-hydrogenation of olefin and aromatic hydrocarbons (see CN1146443A).

CN1152475A discloses a ferric magnetic amorphous alloy catalyst consisting essentially of 45 to 91 wt % nickel, 2 to 40 wt % iron based on the weight of the catalyst and P in balance. The catalyst obtained in this manner has higher catalytic activity than the catalyst described in the CN1073726A.

U.S. Pat. No. 3,839,011 discloses a Raney nickel catalyst and its preparation. The catalyst is prepared by melting nickel and aluminum, pouring the molten alloy into a flowing water stream to be cooled. A readily crushable catalyst of low bulk density is obtained by this process. However, this process cannot provide an amorphous alloy catalyst having an amorphous structure of adequate stability.

U.S. Pat. No. 5,090,997 discloses a process for preparing a Raney nickel catalyst. The catalyst is obtained by heating the molten aluminum alloy to a temperature of 50 to 500° C. above its melting point, atomizing the liquid melt with water or a mixture of water and gas, then cooling the atomized alloy in water or air to obtain a fine particle Raney nickel catalyst. It is difficult to obtain an amorphous catalyst having a higher degree of amorphism by this method owing to its lower cooling rate.

The caprolactam is a main material for producing nylon-6. The purification of caprolactam is a key process for producing caprolactam. The process for producing area Ni(Fe or Co)—Re—P amorphous alloy catalyst by alloying nickel or Fe or Co—Re—P and aluminum using the rapid quenching and moulding method and then leaching out the aluminum with alkali to obtain an amorphous alloy catalyst having a specific surface area of up to 50–130 $m^2/g$ which make it possible to be used in industry. In comparison with Raney nickel catalyst, the Re—Ni—P catalyst has a distinctly higher activity in the saturation-hydrogenation of olefin and aromatic hydrocarbons (see CN1146443A).

CN1152475A discloses a ferric magnetic amorphous alloy catalyst consisting essentially of 45 to 91 wt % nickel, 2 to 40 wt % iron based on the weight of the catalyst and P in balance. The catalyst obtained in this manner has higher catalytic activity than the catalyst described in the CN1073726A.

U.S. Pat. No. 3,839,001 discloses a Raney nickel catalyst and its preparation. The catalyst is prepared by melting nickel and aluminum, pouring the molten alloy into a flowing water stream to be cooled. A readily crushable catalyst of low bulk density is obtained by this process. However, this process cannot provide an amorphous alloy catalyst having a amorphous structure of adequate stability.

U.S. Pat. No. 5,090,997 discloses a process for preparing a Raney nickel catalyst. The catalyst is obtained by heating the molten aluminum alloy to a temperature of 50 to 500° C. above its melting point, atomizing the liquid melt with water or a mixture of water and gas, then cooling the atomized alloy in water or air to obtain a fine particle Raney nickel catalyst. It is difficult to obtain an amorphous catalyst having a higher degree of amorphism by this method owing to its lower cooling rate.

The caprolactam is a main material for producing nylon-6. The purification of caprolactam is a key process for producing caprolactam. The process for producing caprolactam comprises the following steps: benzene hydrogenation to cyclohexane, cyclohexane oxidization to cyclohexanone, cyclohexanone oximation to cyclohexanone oxime and Backmann rearrangement of cyclohexanone-oxime in oleum. The products obtained therefrom include caprolactam and unsaturated compounds. These by-products cannot be removed by extraction and distillation because of their analogical properties. However, the presence of these unsaturated compounds are disadvantageous because they can impair the physical-mechanical properties of the nylon-6 made by polymerizing ε-caprolactam, so they must be removed. During the purification of caprolactam, the unsaturated impurities are saturated by hydrogenation, while their physical-mechanical properties become distinguishable from that of caprolactam, so that these compounds are more easily removed in the subsequent extraction distillation steps. In conventional technology, Raney nickel catalyst is used, but Raney nickel catalyst, with its relatively low activity, larger amount of consumption and limited ability in removing all disturbing impurities, cannot meet the demand of the technological development.

DESCRIPTION OF THE INVENTION

The object of the present invention is to provide a new kind of amorphous alloy hydrogenation catalyst with high activity and high purification capability which has a higher degree of amorphism and higher stability in amorphous state and is particularly useful to hydrorefining of caprolactam, and its preparation.

The hydrogenation catalyst according to the invention comprises essentially Ni ranging between 60 and 98 wt %, Fe ranging between 0 and 20 wt %, one doping metal element selected from the group consisting of chromium, cobalt, molybdenum, manganese and tungsten ranging between 0 and 20 wt %, and aluminum ranging between 0.5 and 30 wt % based on the weight of said catalyst, wherein the weight percentages of iron and the doping element components should not be zero at the same time; and just one broad diffusion peak appears at about 2 θ=45±1° on the XRD patterns of the catalyst within 2 θ range from 20 to 80°.

The catalyst according to the present invention comprises preferably nickel ranging from 70 to 95 wt %, iron ranging from 0.1 to 15 wt %, a metal selected from the group consisting of chromium, cobalt, molybdenum, manganese and tungsten ranging from 0 to 15 wt %, and aluminum ranging from 1 to 15 wt % based on the total weight of said catalyst.

In said catalyst according to the present invention, the nickel content of amorphous alloy is more preferably in the range from 75 to 90 wt %, iron content is more preferably in range from 0.3 to 10 wt %, a metal selected from the group consisting of chromium, cobalt, molybdenum, manganese and tungsten content is more preferably in the range from 0.5 to 8 wt %, and aluminum content is more preferably in the range from 2 to 10 wt % based on the total weight of said catalyst.

The catalyst of the present invention is obtained by allowing the liquid melt of an alloy consisting of 40 to 70 wt % nickel, 30 to <50 wt % aluminum, 0 to 15 wt % iron and 0 to 15 wt % chromium, cobalt, molybdenum, manganese or tungsten to harden rapidly at a cooling rate of >1000° C./sec, preferably >10000° C./sec; heat-treating the rapidly hardened alloy in an atmosphere of an inert gas such as hydrogen, nitrogen and/or argon at a temperature of from about 300 to 900° C., preferably 450 to 750° C., for 0.5 to 5 hours; and then leaching out an adequate portion of aluminum from the heat-treated alloy with an alkaline solution.

In the catalyst of the present invention, nickel as an active constituent exists essentially in the form of amorphous state.

According to the invention, the method for preparing said catalyst comprises substantially the following steps:

(1) Preparation of a parent alloy

The parent alloy is prepared by allowing the liquid melt of an alloy consisting of 40 to 70 wt % nickel, 30 to <50 wt % aluminum, 0 to 15 wt % iron and 0 to 15 wt % chromium, cobalt, molybdenum, manganese or tungsten to harden rapidly at a cooling rate of >1000° C./s, preferably >10000° C./s;

(2) Heat-treatment of the parent alloy

The parent alloy obtained form step (1) is treated in an inert atmosphere selected from argon, hydrogen or nitrogen at 300–900° C. for 0.5–5.0 hours, preferably at 450–750° C. for 1–3 hours;

(3) Activation (treatment with base)

The heat-treated alloy obtained from step (2) undergoes an aluminum leaching-out treatment with an alkaline solution, thereby an adequate portion of aluminum is removed from the alloy by the reaction of the heat-treated alloy with the alkaline solution so that the desired composition of said catalyst according to the invention is obtained; the said alkaline solution can be inorganic or organic base solution, preferably an alkali metal hydroxide aqueous solution, and more preferably sodium hydroxide aqueous solution; the treatment temperature is from ambient temperature to 120° C., a more preferably temperature is 50–100° C.; the treatment time is between 0.5 and 5 hours, more preferably 1–3 hours; the concentration and amount of alkaline solution is not limited, and can be determined based on the desired composition of the catalyst and the existing conditions for preparing Raney nickel catalyst of the prior art; when using aqueous sodium hydroxide, for example, the concentration of aqueous sodium hydroxide can be from 10 to 40 wt %, and then weight ratio of parent alloy/NaOH can be from 1:0.5 to 1:4;

(4) Washing of the catalyst

The sample obtained from step (3) is washed free from alkali and aluminate with water having a temperature of from ambient temperature to 100° C., preferably 60 to 100° C., with the resultant solution having a preferred pH between 7 and 13; the sample washed can be stored in water on ethanol, most preferably under an inert atmosphere.

The catalyst according to the present invention is designed for use in hydrogenation of olefin, alkyne, aromatics, nitro, carbonyl groups, nitrile group and other unsaturated compounds, and especially suitable for hydrorefining of caprolactam.

Figure 1:
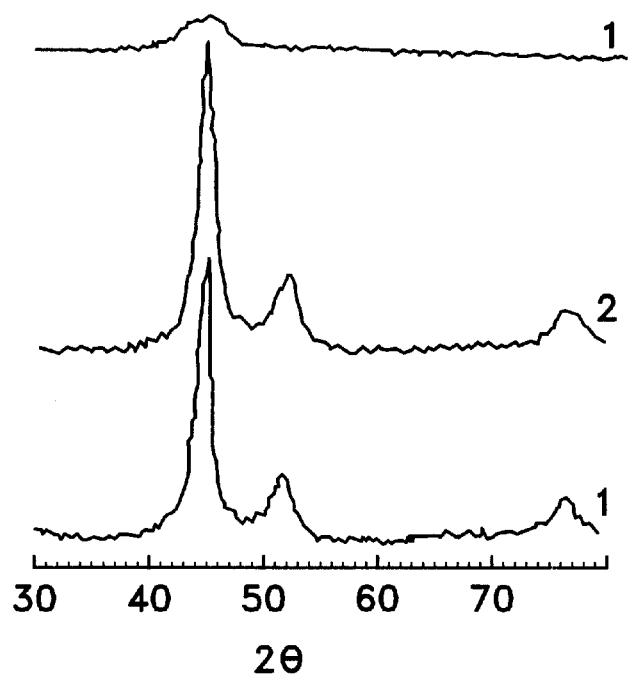
FIG. 1, FIG. 2, FIG. 3 and FIG. 4 are X-ray diffraction (XRD) patterns of the catalysts according to the invention and the comparative catalysts (seen in Example 11).

The catalyst according to the present invention has a distinctly higher hydrorefining activity then conventional Raney nickel catalyst (seen in Example 9), and has higher activity and stability than non heat-treated amorphous catalyst (seen in Examples 10 and 11).

The following examples are presented to further illustrate this invention without any intention of limiting the scope of this invention.

EXAMPLE 1

This example illustrates preparation of Ni—Fe—Mo—Al amorphous alloy catalyst.

49 g of nickel, 49 g of aluminum, 1 g of iron and 1 g of molybdenum were added to a quartz tube heated in a high-frequency furnace to above 1300° C. for liquidation and alloying, and then the liquidated alloy was extruded out by the force of an inert gas from a nozzle at the lower end of the tube onto a rapidly spinning copper roller at a rate of 800 rpm filled with cooling water, and was then cooled down rapidly and thrown out tangentially to form a scaly strip. The strip was ground to particles of about 70 μ in size as a precursor for use. After screening, the parent alloy was heat-treated at a temperature of 600° C. for 3 hours under hydrogen environment. Then, the heat-treated alloy was activated in a three-necked bottle filled with 1000 g NaOH solution with a concentration 20 wt % at a constant temperature of 90° C. for 1 hour with stirring. This liquor was then separated off by decanting and the catalyst was washed with distilled water of 80° C. to a pH of 7. The catalyst, which was numbered Catalyst-1, was stored under water for future use.

EXAMPLES 2–8

The catalysts were prepared according to Example 1, only that the weight ratio of metals, preparation conditions such as heat-treatment temperature, heat-treatment time, alkali-treatment (dealuminum) temperature, alkali-treatment time and washing temperature were changed, the preparation conditions of different catalysts are shown in Table 1, wherein the catalysts of different examples listed are numbered Catalyst-2 to Catalyst-8 respectively.

TABLE 1

Preparation conditions of catalysts.

| Exp. | Composition of parent alloy | Heat treatment Temp. °C | Time hr | Dealuminum activation Alloy/alkali weight ratio | Temp. °C | Time hr | Washing Water Temp. °C | pH Value |
|---|---|---|---|---|---|---|---|---|
| 2 | $Ni_{48}Fe_{1.5}Cr_{2.5}Al_{48}$ | 600 | 3 | 1:1 | 100 | 1 | 80 | 7 |
| 3 | $Ni_{50}Fe_{5.5}Cr_{2.5}Al_{42}$ | 600 | 3 | 1:1 | 100 | 1 | 80 | 7 |
| 4 | $Ni_{48}Fe_{1.5}Mo_{2.5}Al_{48}$ | 600 | 3 | 1:2 | 50 | 1 | 80 | 7 |
| 5 | $Ni_{60}Fe_2Cr_1Al_{37}$ | 700 | 2 | 1:2 | 100 | 1.5 | 100 | 7 |
| 6 | $Ni_{48}Fe_{2.5}Mo_{1.5}Al_{48}$ | 700 | 2 | 1:2 | 100 | 1.5 | 100 | 7 |
| 7 | $Ni_{52}Fe_2Al_{46}$ | 600 | 3 | 1:2 | 90 | 1 | 100 | 7 |
| 8 | $Ni_{52}Cr_2Al_{46}$ | 600 | 3 | 1:2 | 90 | 1 | 100 | 7 |

Comparative Examples 1–4

Comparative example 1 provides a kind of Raney nickel catalyst (Comparative Catalyst-1), which was produced by Jiangsu Yangzhou Catalyst Plant China and kept in water of pH of 13.

Comparative example 2 provides a kind of Raney nickel catalyst (Comparative Catalyst-2), which was produced by the Activated Metals & Chemicals Corporation USA and kept in basic water of pH of 12.

Comparative example 3 provides a kind of catalyst having not been heat-treated (Comparative Catalyst 3), which was prepared by the same method as that for the preparation of Catalyst 2 used in Example 2, except that the parent alloy underwent directly the alkali treatment without going through the heat-treatment in an atmosphere of hydrogen.

Comparative example 4 provides a kind of catalyst having not been heat-treated (Comparative Catalyst 4), which was prepared by the same method as that for the preparation of Catalyst 4 of Example 2, except that the parent alloy underwent directly the alkali treatment without going through the heat-treatment in an atmosphere of hydrogen.

EXAMPLE 9

This example illustrates the hydrorefining activities of the catalysts of the present invention and comparative catalysts in purification of caprolactam.

The purification of caprolactam was carried out by adding 1500 g of caprolactam aqueous solution having a caprolactam content of 30 wt % (having a PM value of 120s) and 1 g of said catalyst of the present invention to a 2000 mL tri-mouth-flask with hydrogen was introduced under ambient pressure at a velocity of 50 L/h heated in a heating jacket and maintained at 90° C., with stirring for 30 min at a rate of 540 rpm. The pellucid liquid product had its permanganate number (=PM number) determined.

The PM number is usually measure of the unsaturated compounds, especially those with varied but smaller amount of components. The PM number is defined as the number of seconds elapsing after the addition of 1.00 mL of 0.002 mol/L potassium permanganate to 100 mL of caprolactam solution of 20° C., which is prepared by adding 10 g of caprolactam solution which has been prepared in advance by adding 6.0 g of caprolactam and a small amount of water to a 200 mL volumetric flask and diluting to mark to a 100 mL dry comparison tube and then adding distilled water to fill the tube to the mark, until the moment at which the color of this solution becomes equal to the color of a standard solution.

The standard solution is prepared by adding 3000 mg of high-purity cobalt nitrate $(Co(NO_3)_2 6H_2O)$ and 12 mg of high-purity potassium dichromate in 1 L water to be diluted and homogenized.

The PM is determined in accordance with "Produce and Application of ε-caprolactam". (Edited by compiler of Produce and Application of ε-caprolactam, Beijing: hydrocarbon process press in 1988).

The hydrorefining activities and the composition of catalysts of examples 1–8 and comparative examples 1–2 are shown in Table 2. These results indicate that the catalysts of this invention demonstrated higher activity than Raney nickel catalyst does.

TABLE 2

Catalytic activities of catalysts in the purification of caprolactam

| | Composition of catalyst | PM |
|---|---|---|
| Catalyst-1 | $Ni_{79}Fe_2Mo_{1.8}Al_{17.2}$ | 800 |
| Catalyst-2 | $Ni_{87}Fe_2Cr_3Al_8$ | 1590 |
| Catalyst-3 | $Ni_{80.5}Fe_8Cr_{3.5}Al_8$ | 1420 |
| Catalyst-4 | $Ni_{82}Fe_5Mo_{3.5}Al_{9.5}$ | 800 |
| Catalyst-5 | $Ni_{88}Fe_{3.5}Cr_{1.5}Al_7$ | 1060 |
| Catalyst-6 | $Ni_{85}Fe_{3.5}Mo_{1.5}Al_{10}$ | 1246 |
| Catalyst-7 | $Ni_{88}Fe_3Al_9$ | 786 |
| Catalyst-8 | $Ni_{88}Cr_3Al_9$ | 872 |
| Comparative-1 | Raney nickel | 310 |
| Comparative-2 | Raney nickel | 618 |

EXAMPLE 10

This example illustrates the effects of thermal treatment on the catalytic activity of amorphous alloy catalyst in hydrogenation.

The purification of caprolactam was carried out in the same manner as in Example 9 using the Comparative Catalysts 3 and 4. The results are shown in Table 3 indicating that heat treatment can improve the catalytic activities of catalysts.

TABLE 3

Effects of thermal treatment on the hydrogenation activities of the catalysts

| No. | Composition of alloy | Heat treatment | Composition of catalyst | PM |
|---|---|---|---|---|
| Catalyst-2 | Ni$_{48}$Fe$_{1.5}$Cr$_{2.5}$Al$_{48}$ | yes | Ni$_{87}$Fe$_2$Cr$_3$Al$_8$ | 1590 |
| Comparative-3 | | no | | 830 |
| Catalyst-4 | Ni$_{48}$Fe$_{1.5}$Mo$_{2.5}$Al$_{48}$ | yes | Ni$_{82}$Fe$_5$Mo$_{3.5}$Al$_{9.5}$ | 800 |
| Comparative-4 | | no | | 728 |

EXAMPLE 11

This example illustrates the XRD properties of the catalyst of the present invention and comparative sample, which explain the effect of heat treatment on the stability in hydrogenation.

The XRD patterns of catalyst-2, Comparative Catalyst-1 and Comparative Catalyst-2 are shown in FIG. 1, where 1 represents Catalyst-2, 2 represents Comparative Catalyst-1 and 3 represents Comparative Catalyst-2.

Figure 2:
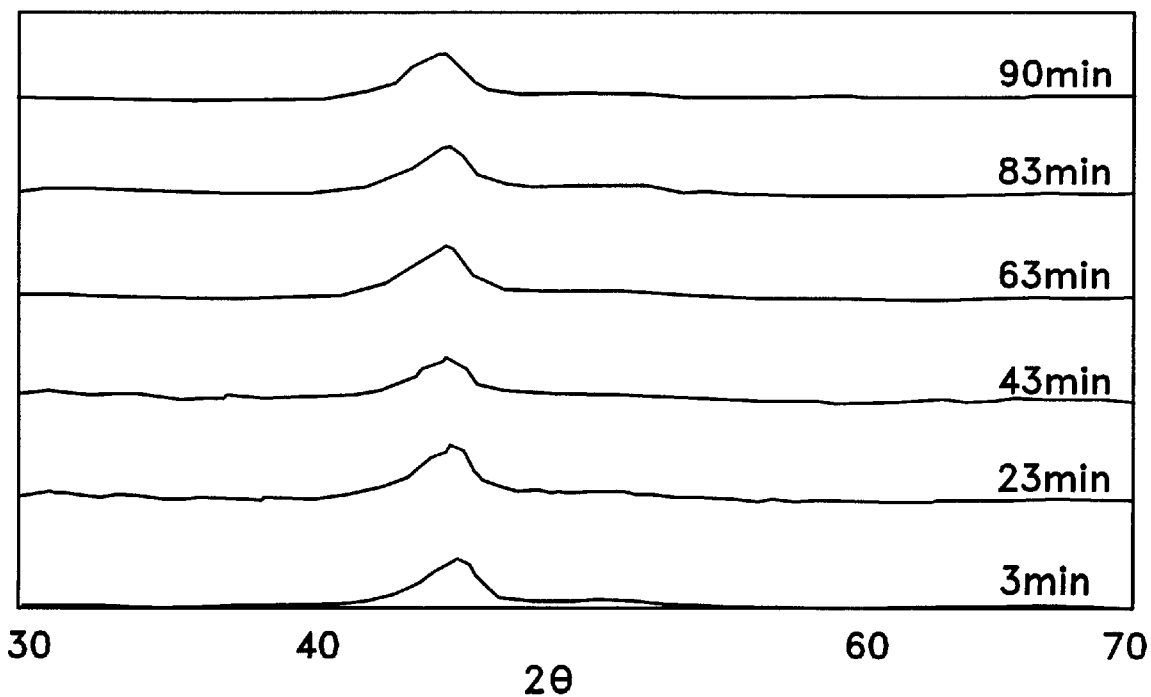

The change of XRD pattern of Catalyst-2 as a function of dealuminum time are shown in FIG. 2.

Figure 3:
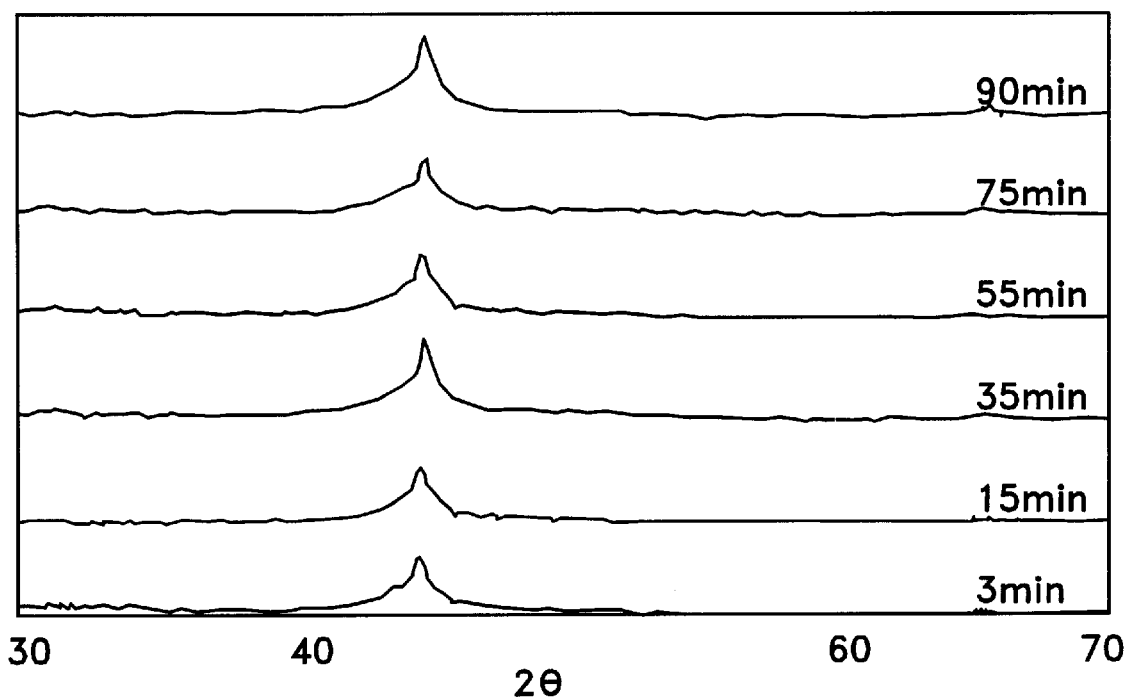

The change of XRD pattern of Comparative catalyst-3 as a function of dealuminum time are shown in FIG. 3.

Figure 4:
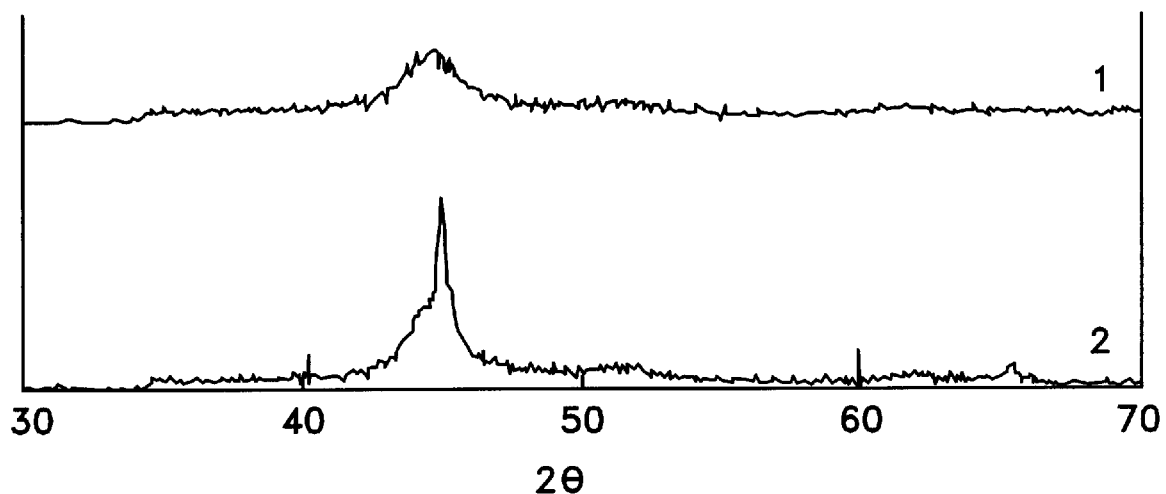

The XRD patterns of Catalyst-2 and Comparative Catalyst-3, which is obtained after a resting period of two months from its preparation, are shown in FIG. 4, wherein 1 represents Catalyst-2 and 2 represents Comparative Catalyst-3.

It is shown that only a broad diffusion peak appears around 2 θ=45° corresponding to amorphous nickel is observed in the XRD pattern of catalyst according to the invention in FIG. 1. In the XRD patterns of Raney nickel, however, there are three sharp diffraction peaks at 2 θ≈45°, 2 θ≈52° and 2 θ≈56° resulting from crystalline nickel.

It can be seen from FIG. 2 and FIG. 3 that, after heat treatment, the catalyst of this invention has attained a higher degree of amorphism.

From FIG. 4, it can be seen that catalysts after heat treatment remain in an amorphous state after 2 months of storage see the broad diffusion peak; however, the catalyst without heat treatment appears sharp peak from crystallization.

What is claimed is:

1. An amorphous alloy catalyst for hydrogenation essentially consisting of Ni ranging between 60 and 98 wt %, Fe ranging between 0 and 20 wt %, one doping metal element selected from the group consisting of chromium, cobalt, molybdenum, manganese and tungsten ranging between 0 and 20 wt %, and aluminum ranging between 0.5 and 30 wt % based on the weight of said catalyst, wherein the weight percentages of said iron and said doping metal element component may not be zero at the same time; wherein said catalyst has just one broad diffusion peak appearing at about 2 θ≈45±1° on the XRD patterns of the catalyst within 2 θ range from 20 to 80°.

2. The catalyst of claim 1, wherein said catalyst is obtained by allowing the liquid melt of an alloy consisting of 40 to 70 wt % nickel, 30 to <50 wt % aluminum, 0 to 15 wt % iron and 0 to 15 wt % chromium, cobalt, molybdenum, manganese or tungsten to harden rapidly at a cooling rate of >1,000° C./sec, heat-treating the rapidly hardened alloy in an atmosphere of an inert gas at a temperature within the range from 300 to 900° C. for a time of between 0.5 and 5 hours, and then leaching out an adequate portion of aluminum from the heat-treated alloy with alkaline solution.

3. The catalyst of claim 2, wherein said cooling rate is >10,000° C./sec.

4. The catalyst of claim 2, wherein said heat-treating is conducted at a temperature of 450–750° C. for 0.5–5 hours.

5. The catalyst of claim 1, wherein said catalyst consists of nickel ranging between 70 and 95 wt %, iron ranging between 0.1 and 15 wt %, one metal element selected from the group consisting of chromium, cobalt, molybdenum, manganese and tungsten ranging between 0 and 15 wt %, and aluminum ranging between 1 and 15 wt % based on the weight of said catalyst.

6. The catalyst of claim 5, wherein said catalyst consists of nickel ranging between 75 and 90 wt %, iron ranging between 0.3 and 10 wt %, one metal element selected from the group consisting of chromium, cobalt, molybdenum, manganese and tungsten ranging between 0.5 and 8 wt %, and aluminum ranging between 2 and 10 wt % based on the weight of said catalyst.

7. The catalyst of claim 1 wherein said nickel exists essentially in the form of amorphous state.

8. A method for preparing said catalyst of claim 1, comprising:

(1) allowing the liquid melt of an alloy consisting of 40 to 70 wt % nickel, 30 to <50 wt % aluminum, 0 to 15 wt % iron and 0 to 15 wt % chromium, cobalt, molybdenum, manganese or tungsten to harden rapidly at a cooling rate of >1000° C./sec;

(2) heat-treating the hardened alloy obtained from step (1) in an inert gas atmosphere at a temperature of from 300 to 900° C. for 0.5 to 5 hours;

(3) Leaching out an adequate portion of aluminum from the heat-treated alloy obtained from step (2) with an alkaline solution by reacting the alloy with the alkaline solution so that the composition of the catalyst meets that defined in claim 1;

(4) washing the alkaline-treated alloy obtained from step (3) with water having a temperature of between 20 and 100° C. so that the resultant washed solution having a pH between 7 and 13.

9. The method of claim 8, wherein said heat-treating in step (2) is conducted at a temperature of 450–750° C. for 1 to 3 hours.

10. The method of claim 8 wherein said alkaline solution used in step (3) is sodium hydroxide aqueous solution, and said leaching out is conducted at a temperature of from ambient temperature to 120° C. for 0.5–5 hours.

11. The method of claim 10, wherein said leaching-out is conducted at temperature of 50–100° C.

12. The method of claim 8, wherein the temperature of water for washing in step (4) is in the range of 60 to 100° C.

* * * * *